United States Patent
Franke et al.

(10) Patent No.: US 11,169,233 B2
(45) Date of Patent: Nov. 9, 2021

(54) HYBRID MPI AND MRI/CT IMAGING APPARATUS AND METHOD

(71) Applicant: Bruker BioSpin MRI GmbH, Ettlingen (DE)

(72) Inventors: Jochen Franke, Karlsruhe (DE); Volker Niemann, Ispringen (DE)

(*) Notice: Subject to any disclaimer, the term of this patent is extended or adjusted under 35 U.S.C. 154(b) by 0 days.

(21) Appl. No.: 17/074,176

(22) Filed: Oct. 19, 2020

(65) Prior Publication Data
US 2021/0116525 A1    Apr. 22, 2021

(30) Foreign Application Priority Data
Oct. 17, 2019    (DE) .......................... 102019216041.7

(51) Int. Cl.
*G01R 33/48*    (2006.01)
*G01R 33/34*    (2006.01)
(Continued)

(52) U.S. Cl.
CPC ........ *G01R 33/4812* (2013.01); *A61B 5/0035* (2013.01); *A61B 5/055* (2013.01);
(Continued)

(58) Field of Classification Search
CPC .............. G01R 33/4812; G01R 33/383; G01R 33/34007; A61B 5/0035; A61B 5/0515;
(Continued)

(56) References Cited

U.S. PATENT DOCUMENTS

| | | | |
|---|---|---|---|
| 4,355,236 A | 10/1982 | Holsinger | |
| 8,884,617 B2 * | 11/2014 | Goodwill | ........... G01R 33/1276 324/301 |

(Continued)

FOREIGN PATENT DOCUMENTS

| | | |
|---|---|---|
| DE | 102015218122 B3 | 9/2016 |
| EP | 1876462 A1 | 1/2008 |

(Continued)

OTHER PUBLICATIONS

Vogel, Patrick, et al. "Magnetic particle imaging meets Computed Tomography: first simultaneous imaging". Scientific Reports, 2019.

*Primary Examiner* — Dixomara Vargas
(74) *Attorney, Agent, or Firm* — Benoit & Côté Inc.

(57) ABSTRACT

A hybrid imaging apparatus for imaging an object to be examined located in a sample volume can be operated in an MPI mode and in at least one further imaging mode and comprises a magnet arrangement embodied to generate, in the MPI mode, a magnetic field with a gradient B1 and a field-free region in the sample volume, wherein the magnet arrangement comprises a ring magnet pair with two ring magnets in a Halbach dipole configuration, which are arranged coaxially on a common Z-axis that extends through the sample volume, wherein the ring magnets are arranged so as to be twistable relative to one another about the Z-axis. Consequently, it is possible to generate magnetic fields that meet the requirements of both MRI and MPI such that the hybrid imaging apparatus can be equipped for measurements in various imaging modes, including MPI, MRI and CT.

15 Claims, 7 Drawing Sheets

(51) Int. Cl.
*G01R 33/383* (2006.01)
*A61B 5/0515* (2021.01)
*A61B 6/00* (2006.01)
*A61B 6/03* (2006.01)
*A61B 5/055* (2006.01)
*A61B 5/00* (2006.01)

(52) U.S. Cl.
CPC ............ *A61B 5/0515* (2013.01); *A61B 6/032* (2013.01); *A61B 6/4417* (2013.01); *A61B 6/5247* (2013.01); *G01R 33/34007* (2013.01); *G01R 33/383* (2013.01)

(58) Field of Classification Search
CPC ....... A61B 5/055; A61B 6/032; A61B 6/4417; A61B 6/5247
See application file for complete search history.

(56) References Cited

U.S. PATENT DOCUMENTS

| | | | |
|---|---|---|---|
| 9,274,084 B2* | 3/2016 | Goodwill | G01R 33/10 |
| 9,763,594 B2* | 9/2017 | Goodwill | A61B 5/0515 |
| 10,261,141 B2* | 4/2019 | Tonyushkin | A61B 5/0515 |
| 10,656,224 B2 | 5/2020 | Buzug et al. | |
| 10,667,716 B2* | 6/2020 | Goodwill | G01N 27/72 |
| 2011/0221438 A1* | 9/2011 | Goodwill | G01N 27/72 324/301 |
| 2015/0015247 A1* | 1/2015 | Goodwill | G01R 33/10 324/244 |
| 2015/0177343 A1 | 6/2015 | Wald et al. | |
| 2016/0135710 A1* | 5/2016 | Goodwill | A61B 5/0515 600/409 |
| 2018/0206757 A1* | 7/2018 | Goodwill | A61B 5/0515 |
| 2018/0335487 A1* | 11/2018 | Tonyushkin | G01R 33/1276 |
| 2020/0245893 A1* | 8/2020 | Goodwill | G01R 33/1276 |
| 2020/0289839 A1* | 9/2020 | Hensley | G16H 30/20 |
| 2021/0255263 A1* | 8/2021 | Franke | G01R 33/445 |

FOREIGN PATENT DOCUMENTS

| | | |
|---|---|---|
| EP | 2957220 A1 | 12/2015 |
| WO | 2017083849 A1 | 5/2017 |

* cited by examiner

HYBRID MPI AND MRI/CT IMAGING APPARATUS AND METHOD

BACKGROUND OF THE INVENTION

Field of the Invention

The invention relates to a hybrid imaging apparatus for imaging an object to be examined located in a sample volume, wherein the hybrid imaging apparatus can be operated in an Magnetic Particle Imaging (MPI) mode and in at least one further imaging mode and comprises a magnet arrangement embodied to generate, in the MPI mode, a magnetic field with a gradient B1 and a field-free region in the sample volume. The invention also relates to a method for designing a magnet arrangement for use in a hybrid imaging apparatus, and a method for combined recording of image data by means of at least one further imaging method, selected from Magnetic Resonance Imaging (MRI) and Computed Tomography (CT).

Description of the Related Art

A hybrid imaging apparatus for imaging an object by means of MPI and a further imaging mode is known from patent document EP 2 957 220 A1.

Hybrid imaging apparatuses serve to measure a sample by means of a plurality of imaging processes, ideally without removing the sample from the sample position. As a result, it is possible to use different methods to obtain information items not only about the same sample but, in particular, from the same location of the sample.

In magnetic particle imaging (MPI), local concentrations of magnetizable nanoparticles are ascertained in the interior of an object. These nanoparticles are periodically magnetized by an MPI excitation field (drive field) that is periodically altered with a predetermined frequency. For the spatial encoding, the magnetic excitation field is superposed with a time-constant selection magnetic field which has a field-free region. Proceeding from this field-free region, the selection magnetic field increases quickly, and so magnetizable nanoparticles reach magnetic saturation at already a small distance from the field-free region. Therefore, the MPI measurement signal originates from the local surroundings of the field-free region and provides information about the local particle concentration present there. Thus, a magnetic field with a gradient B1 and a field-free region must be made available for MPI measurements. By contrast, a static, homogeneous main magnetic field which is used to polarize the nuclear magnetization is used in the case of magnetic resonance imaging (MRI) measurements. Therefore, as a rule, an MRI magnet arrangement cannot be used for MPI measurements, and vice versa.

Patent document US 2015/0177343 A1 discloses a portable magnet arrangement for MRI measurements, which comprises a magnet arrangement with a permanent magnet for generating the main magnetic field. The magnet arrangement can be rotated about its axis. A magnetic field usable for MPI measurements cannot be generated using this magnet arrangement.

Patent document WO 2017/083849 A1 has disclosed a system that allows magnetic resonance images and computed tomography images of an object to be recorded at the same time. While an object is recorded, x-ray source and x-ray detector and also permanent magnets for generating an MRI main magnetic field can be rotated about the object at the same time. However, MPI measurements cannot be carried out using the apparatus disclosed in WO 2017/083849 A1.

As means for generating the main magnetic field required for the MRI, WO 2017/083849 A1 uses, inter alia, permanent magnets in a Halbach configuration. In the case of a Halbach ring, the magnetization direction of the lateral ring side has a continuous rotation along the lateral profile in the plane perpendicular to the ring axis, wherein the magnetization direction returns to its initial value after one revolution around the entire lateral ring side.

The use of Halbach rings is also known for generating magnetic fields for focusing particle beams in storage rings (as shown, for example, in patent document U.S. Pat. No. 4,355,236 A. To this end, the apparatus disclosed in U.S. Pat. No. 4,355,236 A discloses a plurality of Halbach rings, which can be twisted relative to one another.

DE 10 2015 218 122 B3 describes the use of Halbach rings for generating an MPI magnetic field. In order to achieve a rotation of the field-free line, the magnet arrangement consisting of the Halbach rings is rotated about an axis. MRI measurements and CT measurements cannot be carried out using this arrangement.

An arrangement allowing MPI measurements and CT measurements to be carried out simultaneously is known from patent document EP 2 957 220 A1. There, the MPI selection field is generated by means of a coil arrangement. However, a homogeneous main magnetic field usable for MRI measurements cannot be generated using this magnet arrangement.

SUMMARY OF THE INVENTION

The present invention involves a hybrid imaging apparatus, with which it is possible to generate magnetic fields that meet the requirements of both MRI and MPI such that the hybrid imaging apparatus can be equipped for measurements in various imaging modes, including MPI, MRI and CT.

According to the invention, this is achieved by a hybrid imaging apparatus, by a method for designing a magnet arrangement for use in a hybrid imaging apparatus, and by methods for combined recording of image data of a plurality of imaging methods.

In the hybrid imaging apparatus according to the invention, the magnet arrangement comprises a ring magnet pair with two ring magnets in a Halbach dipole configuration, which are arranged coaxially on a common Z-axis that extends through the sample volume. In practice, these are realized by discrete magnet segments, which have a magnetization that gradually varies with the angle. Each ring magnet has a dipole magnetization direction, which corresponds to the direction of the magnetic field in the interior of the ring magnet. The dipole magnetization direction of each ring magnet extends perpendicular to the Z-direction (i.e., in the XY-plane). A cylindrical magnet object is also understood to be a ring magnet.

According to the invention, the ring magnets are arranged so as to be twistable relative to one another about the Z-axis and can be rotated individually (in mechanically decoupled fashion). The coaxially arranged ring magnets can be brought into different configurations (different angle positions of the dipole magnetization directions of the two ring magnets) by being twisted against one another about the common axis.

As a result of the twistability of the individual rings against one another according to the invention, it is possible to influence the type of magnetic field (homogeneous magnetic field, magnetic field gradient). This allows magnetic fields to be generated, which can be used for different applications (for example, MPI, MRI). This facilitates the use of different measurement processes with different magnetic field requirements within one imaging apparatus.

In the MPI mode, the ring magnets of the ring magnet pair have an antiparallel dipole magnetization direction. In the MPI mode, the ring magnet pair generates a field-free region, preferably as a field-free line orthogonal to the Z-axis. This can be achieved by virtue of using ring magnets that are structurally identical in terms of dimensioning and magnetizing, wherein the ring magnets are aligned with respect to one another such that the dipole fields generated by the two ring magnets are aligned in opposite directions. That is to say, the dipole axes (dipole magnetization directions) of the two ring magnets of the ring magnet pair are twisted by 180° against one another (antiparallel dipole magnetization directions).

Further devices belonging to the magnetic device allow the field-free line generated by the ring magnet pair to be "modified", for example by a superposition with other magnetic fields, in particular by a shift of the field-free line such that a field-free region that deviates from the field-free line generated by the ring magnet pair arises.

The magnet arrangement defines a coordinate system X'Y'Z that rotates about the Z-axis. The dipole magnetization direction of one of the ring magnets of the ring magnet pair defines the X'-direction. In the MPI mode, the dipole magnetization direction of the other ring magnet of the ring magnet pair is aligned in the –X'-direction. A field-free line generated by the ring magnet pair is consequently aligned in the Y'-direction (elongate extent of the field-free line in the Y'-direction).

To generate at least a magnetic excitation field, the hybrid imaging apparatus according to the invention comprises an MPI excitation coil system (drive field). The MPI excitation coil system is preferably operated with electrical resonance and moves the field-free region through the sample volume with an excitation frequency f1 in the range of 1 kHz to 300 kHz. The MPI excitation coil system can be a combined excitation and detection coil system.

Preferably, the MPI excitation coil system is a mechanically static excitation coil system (i.e., an excitation coil system that neither rotates nor is shifted within the apparatus), which is configured to generate a magnetic field with a field direction in the direction of the Z-axis. As an alternative to an excitation coil system that generates a magnetic field with a field direction in the direction of the Z-axis, use can also be made of an excitation coil system which is configured to generate a magnetic field with a field direction orthogonal to the extent of the field-free line (for example, in the X'-direction). However, such an excitation coil system would have to be co-rotated in the case of a rotation of the ring magnet pair. Preferably, transmit-receive coils are used as the MPI excitation coil system such that measurement signals can also be received by the MPI excitation system. Alternatively, use can also be made of dedicated excitation coils and receiver coils. The MPI excitation coil system is preferably arranged axially between the ring magnets of the ring magnet pair.

In a preferred embodiment, the MPI excitation coil system is used in combination with a shift field coil system (focus field), for the following reason: the field-free region is the sensitive area from which MPI signals can be received. If this area is driven with a high frequency by the excitation field (drive field), the tracers (e.g., superparamagnetic iron oxide particles) situated in the FoV (i.e., in the sensitive/reconstructed imaging region) are excited. If the field-free region is present in the form of a field-free line, it is consequently possible to measure projections of the tracer distribution along the field-free line. For MPI imaging, projections must be determined over the entire FoV for a multiplicity of angle settings of the magnetic arrangement about the Z-axis. This is not achievable by an MPI excitation coil system on its own in the case of a magnetic field with a strong gradient B1 because, otherwise, the amplitude of the drive field generated by the excitation coil system would have to be very large; however, this is linked to negative effects on the object to be examined since high amplitudes may lead to peripheral nerve stimulation (PNS), e.g., nerve twitching or the like, or to tissue heating by way of the so-called specific absorption rate (SAR). A preferred embodiment of the hybrid imaging apparatus according to the invention therefore provides for the apparatus to comprise a shift field coil system (focus field), which is configured to shift the field-free region at least along a spatial direction, preferably along all spatial directions, within the sample volume in quasi-static fashion (i.e., in discrete steps) or with a shift frequency (i.e., the continuous wave (CW) mode). The shift field brings about an offset of the field-free region, preferably in the excitation direction; as a result, it is possible to reduce the required drive field amplitude of the excitation field. The shift of the field-free region by way of the shift field coil system is implemented incrementally (discretely) or with a shift frequency f2 which is less than the excitation frequency (in particular f2=DC-5 kHz) such that an excitation scan can be carried out by means of the excitation coil system at each shift brought about by the shift field. In the case of a field-free line as field-free region, it is advantageous if the shift field magnetic coil system is designed such that there is a shift perpendicular to the elongate extent of the field-free line.

Preferably, all ring magnets of the magnet arrangement are mechanically couplable such that the magnet arrangement as a whole is rotatable about the Z-axis. Common twisting of the ring magnets allows the field-free region to be rotated in the FoV. This rotation can be implemented discretely or continuously with a rotation frequency f3 in the region of DC-200 Hz and it is used to record different projection angles.

In a special embodiment of a hybrid imaging apparatus according to the invention, the field-free region in the MPI mode is a field-free line.

In a particularly preferred embodiment of the hybrid imaging apparatus according to the invention, the further imaging mode is an MRI mode for recording magnetic resonance imaging images, wherein the magnet arrangement is embodied to generate a B0-field with a B0-isocenter, suitable for MRI measurements, by virtue of the dipole magnetization directions of the ring magnets within the ring magnet pair being aligned parallel to the XY-plane in the MRI mode. Thus, the two ring magnets of the ring magnet pair are not twisted with respect to one another in the MRI mode. In the MRI mode, the dipole magnetization directions of the ring magnets of the magnet arrangement are aligned in mirror symmetric fashion with respect to the XY-plane (which extends through the center of the magnet arrangement).

To carry out the MRI measurements, this embodiment of the hybrid imaging apparatus according to the invention comprises an MRI gradient system of at least first order and an MRI excitation coil system with an RF excitation coil for signal excitation and detection. Further, dedicated receiver coils can also be used. A B0-field suitable for MRI measurements must be homogeneous in an examination region (ROI—region of interest), in particular with deviations of the order of 1 to 100 ppm of the field amplitude obtained. In the MRI mode, the B0-field amplitude should be maximized within the ROI where possible and, in particular, should be in the range of 0.1 T to 2 T. Since the manufacturing accuracies of the components are insufficient, the hybrid imaging apparatus according to the invention preferably moreover comprises a shim apparatus, in particular a shim tube (for basic homogenization) arranged coaxially to the Z-axis and higher-order shim coils (in particular, 2nd-6th order) for homogenizing the magnetic field generated by the magnet arrangement in the MRI mode. The MRI shim apparatus (passive=shim tube and active=shim coils) serves to homogenize the magnetic field generated by the magnet arrangement and to compensate field distortions by the examination object itself. In the first order, the magnetic field generated by the magnet arrangement is homogenized by the MRI gradient coils system (i.e., the gradient system generates a magnetic field which eliminates the first order magnetic field components of a mathematical expansion of the magnetic field (B1-component)). A homogenization of the magnetic field in higher orders (in particular, in the 2nd to 6th order) can be implemented by the shim coils systems. Using the two active/adjustable shim apparatuses (i.e., MR gradient coils system and MRI shim coils system), it is possible to also compensate the influences of the object to be examined. A basic homogenization (i.e., compensation of production-related deviations, for example in respect of the magnetization direction of individual partial segments of the ring magnets, positioning of the individual partial segments with respect to one another, defects in the basic material of the partial segments, arrangement and mounting of the ring magnets, alignment (rotation, tilt in the XY-plane) of the magnetic rings with respect to one another) can be realized by passive shim tubes. The shim tube is preferably arranged axially between the ring magnets of the ring magnet pair, at least in part. The shim coils can be deactivated in the MPI configuration; however, the fixed values of the shim tube cannot be altered and have a direct influence on the MPI gradient field and hence on the field-free region. Usually, a combination of all three options is used. Then, the shim apparatus comprises both active and passive components.

A further embodiment of the hybrid imaging apparatus according to the invention provides for the further imaging mode to be a CT mode for recording computed tomography images, wherein the ring magnets of the ring magnet pair are spaced apart from one another in the Z-direction and the apparatus comprises a CT unit with an x-ray source and an x-ray detector opposite to the x-ray source, wherein x-ray source and x-ray detector are mounted in the XY-plane in a manner rotatable about the Z-axis. The CT unit is axially arranged between the ring magnets of the ring magnet pair and rotates about the Z-axis in the CT mode.

Preferably, x-ray source and x-ray detector are mechanically couplable to the magnet arrangement in such a way that the CT unit is rotatable about the Z-axis together with the magnet arrangement. Coupling the rotation of the magnet arrangement and the rotation of the CT unit can reduce the stray magnetic field problem which arises on account of a changing magnetic field (induced by a relative movement between magnetic field arrangement and CT unit) through which the electron beam of the CT unit would otherwise pass. The static stray magnetic field of the magnetic field arrangement can be compensated or considered directly, and so the electron beam accurately impinges on the anode material.

Preferably, the hybrid imaging apparatus according to the invention is configured to be operated in more than two imaging modes, e.g., MPI, MRI, and CT.

The invention also relates to a method for combined recording of MPI and CT data using an imaging apparatus as described above, wherein the magnet arrangement and the CT unit are rotated together about the Z-axis. To this end, the magnet arrangement is operated in a mode with an arrangement, defined in advance, of the ring magnets with respect to one another (relative ring magnet position), e.g., in the MPI mode. As a result of the common rotation of the magnet arrangement and the CT unit, the electron beam of the x-ray source is always in the same magnetic surroundings during the rotation and, as a result, said electron beam always experiences the same deflection.

Preferably, the MPI and CT data are acquired simultaneously. Then, CT mode and MPI mode are activated at the same time. The selection field generated by the magnet arrangement in the MPI mode does not interfere with the CT recording, and so simultaneous data acquisition can occur without problems.

In a special variant of this method, the MPI data are acquired from a 2D MPI acquisition plane of the sample volume and the CT unit generates an x-ray beam in a CT beam path in the form of a plane or, if a 2D detector is used, an x-ray cone beam, wherein the MPI acquisition plane at least partly overlaps with the CT beam path. Consequently, data can be acquired not only simultaneously but also at the same location using the two modalities. Here, the field-free region in the MPI acquisition plane is shifted.

Preferably, the combined MPI-CT recording is carried out in the form of a helical scan, wherein the CT unit is rotated about the Z-axis together with the magnet arrangement and the MPI excitation coil system such that the field-free region rotates while the object to be examined is moved continuously in the Z-direction through the FoV of the hybrid imaging apparatus or (for the MPI data acquisition) the field-free region is shifted in the Z-direction using auxiliary coils (AC or DC). Consequently, 3D imaging using both modalities can be realized.

The invention also relates to a method for combined recording of MPI data in the MPI mode and of MRI data in the MRI mode using an above-described apparatus, wherein MPI data and MRI data are recorded in succession (sequentially). The ring magnets of the ring magnet pair are twisted against one another for the purposes of switching between the MRI mode and MPI mode.

In the case of a symmetric embodiment of the ring magnets, the field-free region in the MPI mode is located at the same position as the MRI isocenter in the MRI mode. Consequently, the object can be measured at the same location sequentially by both modalities without the object having to be moved. All that is required to this end is a change in configuration of the magnet arrangement: As a result of a twist of the ring magnets against one another within the ring magnet pair, it is possible to change the field topology from the MPI mode to the MRI mode, and vice versa. In the ideal case, the ring magnets of the ring magnet pair are twisted through 180° with respect to one another in order to alternate between the MPI mode and the MRI mode. Depending on manufacturing tolerances, the difference between the two positions may deviate from 180°.

Preferably, a plurality of calibration steps is carried out prior to the data acquisition in the MRI mode in order to improve the image quality. These include, inter alia, the adjustment of active B0-shim channels of the shim apparatus, of the RF pulse power of the excitation coil system and of the receiver gain of a receiver coil system.

The invention also relates to a method for combined recording of CT data in the CT mode and of MRI data in the MRI mode using an above-described apparatus, wherein the B0-isocenter and the CT beam path overlap at least partly one another. The magnet arrangement, the x-ray source (CT tube), and the CT detector are rotated together about the Z-axis, at least in the CT mode, for the purposes of capturing spatial encoding. The CT data and the MRI data are acquired sequentially, respectively in the CT mode and in the MRI mode. As a result of the coincidence of the MRI-B0-isocenter and the CT beam path, it is possible to sequentially acquire data at the same location using the two modalities. Further, the rotation of the magnet arrangement and hence the change in the B0-field direction can be used for direction-dependent MRI sequences. To this end, at least the passive shim unit (shim tube) and the MRI gradient system must be correspondingly co-rotated in addition to the magnet arrangement. Depending on the embodiment, the CT acquisition must be carried out in a certain Halbach ring arrangement (MRI or MPI mode) in order to take account of the stray magnetic field influences on the electron beam of the x-ray source. To this end, an intermediate step may be necessary between recording CT data and recording MRI data in order to change the configuration of the magnet arrangement. As a result of a twist of the two ring magnets of a ring magnet pair against one another, it is possible to change the field topology from the MPI mode to the MRI mode, and vice versa.

For the 3D CT imaging, either a cone beam and a 2D detector or an additional mechanical shift of the object is necessary. In a special variant, the combined MRI-CT recording is carried out in the form of a helical scan, wherein the CT unit is rotated about the Z-axis together with the magnet arrangement while the object to be examined is moved continuously in the Z-direction through the FoV of the hybrid imaging apparatus. Consequently, 3D imaging using both modalities can be realized.

In a special embodiment, the shim system and gradient system are static. The MRI mode is then carried out in a position of the ring magnets at a dedicated angle with respect to the magnetic alignment of the shim system and gradient system. As an alternative thereto, the shim apparatus and the MRI gradient system can be configured in such a way that these can be rotated about the Z-axis.

According to the invention, the ring magnets can be rotated about the Z-axis either simultaneously (mechanically coupled) or individually (mechanically decoupled). A mechanically coupled rotation facilitates a mechanical rotation of the field-free region in the MPI mode or the rotation of the B0-field direction in the MRI mode. A mechanically decoupled rotation facilitates the change of the ring magnet configuration (transfer from the MRI mode to the MPI mode and vice versa). By adapting the ring magnet parameters (ring spacing, internal and external diameter, ring thickness, ring material, ring segmentation, segment magnetization directions, ring angle of attack, etc.), it is possible to optimize the B0-field homogeneity and/or B1-gradient linearity and the rest position of the field-free region. On account of the distance between the ring magnets, it is possible to facilitate further examination processes, such as, e.g., CT or optical methods, at the same location and, where applicable, simultaneously. Consequently, an object can be measured by all modalities at the same location without the sample having to be moved.

The invention also relates to method for designing a magnet arrangement for use in an above-described hybrid imaging apparatus with an MPI mode and an MRI mode, wherein the magnet arrangement comprises ring magnets with a central bore. The method according to the invention includes the following steps:

a. specifying a target magnetic field B0 in the MRI mode and in the MPI mode a target gradient B1 of a magnetic field B to be generated by the magnet arrangement, and an internal diameter of the central bore of the ring magnet pair;

b. specifying the homogeneity of the magnetic field in the sample volume to be generated by the magnet arrangement in the MRI mode by virtue of setting to zero at least the first field order of a mathematical expansion of the magnetic field to be generated by the magnet arrangement, and specifying the linearity of the magnetic field in the sample volume to be generated by the magnet arrangement in the MPI mode by virtue of setting to zero at least the second field order of the mathematical expansion of the magnetic field to be generated by the magnet arrangement;

c. determining free design parameters, in particular geometry parameters of the ring magnets and the distance between the ring magnets by minimizing the volume of the ring magnets under the constraints of steps a) and b) by means of an optimization process.

The method according to the invention comprises a coupled optimization; i.e., identical free design parameters are used in the optimization method for the constraint relating to the MPI mode and for the constraint relating to the MRI mode. Thus, the magnet arrangement is simultaneously optimized in respect of the magnetic field required for the MPI mode and in respect of the magnetic field required for the MRI mode. Further, individual parameters can be weighted differently in order, for example, to prefer the homogeneity requirement in the MRI mode within the optimization. The mathematical expansion is preferably a "central expansion", i.e., an expansion which converges in the direct surroundings of the point of expansion (in general, the magnet center).

In step b), a desired homogeneity for the magnetic field in the MRI mode and desired linearity for the magnetic field in the MPI mode are specified. In the MRI mode, the B0-field should be as homogeneous as possible in the ROI; in particular, deviations should be of the order of 1 to 100 ppm of the field amplitude obtained. Where possible, the B0-field amplitude in the ROI should be maximized in the MRI mode, in particular between 0.1 T and 2 T. In the MPI mode, the magnetic field gradient B1 should have a value ranging from 1 T/m to 20 T/m. The greater the magnetic field gradient B1, the sharper the field-free region and hence the sharper the point spread function of the particle response or the spatial resolution in the image space becomes. Moreover, in step b), stray magnetic field properties of the magnetic field to be generated by the magnet arrangement can be determined outside of the magnet arrangement and can be included in the optimization process. Stray magnetic field properties comprise, in particular, the extent of the magnetic field to be generated by the magnet arrangement found outside of the magnet arrangement. To this end, a far field expansion is preferably used, i.e., an expansion that converges outside of the magnet arrangement.

In particular, the geometric parameters of the ring magnets specified in step c) are: external diameter, ring strength, material of the ring magnets, magnetization, discretization or structure, number of segments of the ring magnets, and magnetization of the segments. Preferably, the minimum weight of the ring magnets is determined as a function of the design parameters determined in step c).

The ring magnets can be manufactured accordingly using the design parameters determined thus, wherein the ring magnets, as a rule, are constructed from individual segments that are permanently adhesively bonded to one another. Moreover, the ring magnets are mechanically interconnected in such a way that they are rotatable against one another about the Z-axis.

Further advantages of the invention are apparent from the description and the drawing. The aforementioned features and the features mentioned further below can likewise be employed, according to the invention, in each case by themselves or in any desired combination. The embodiments shown and described should not be understood to be an exhaustive list, but rather have an exemplary character for the purpose of illustrating the invention.

DETAILED DESCRIPTION

Figure 1:
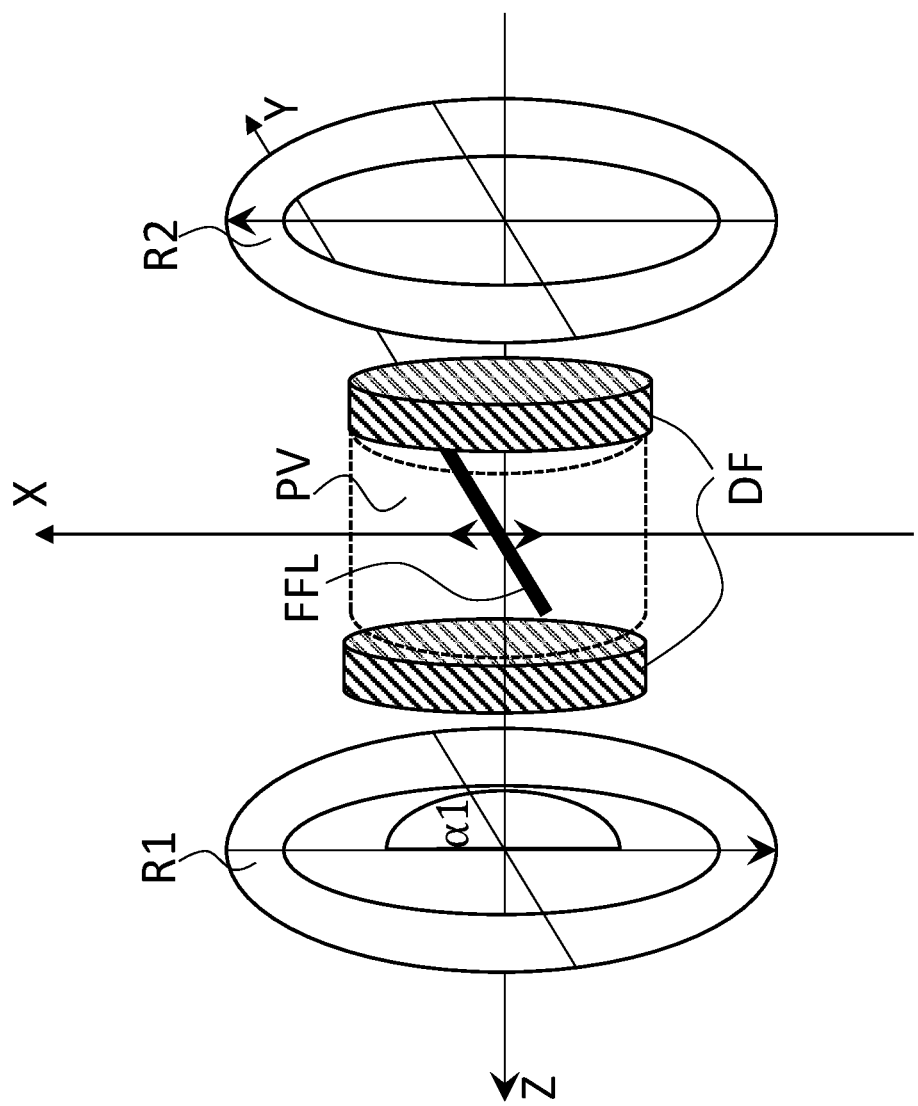
FIG. 1 shows a magnet arrangement and an MPI excitation coil system of a hybrid imaging apparatus according to the invention with antiparallel dipole magnetization directions of the ring magnets in the X-direction.

FIG. 1 shows a magnet arrangement for a hybrid imaging apparatus according to the invention. The magnet arrangement shown in FIG. 1 comprises two ring magnets R1, R2, which form a first ring magnet pair R1/R2. The ring magnets R1, R2 are second-order Halbach rings (k=2, directed dipole moment). The two ring magnets R1, R2 are arranged coaxially with respect to a Z-axis and symmetrically about a sample volume PV, through which the Z-axis extends. The sample volume PV is defined by the freely accessible bore (tube diameter). The dipole magnetization directions of the two ring magnets R1, R2 are twisted by 180° against one another (antiparallel). As a result, a field-free region in the form of a line arises (field-free line FFL). In order to move the field-free line FFL within the sample volume PV, provision is made of an MPI excitation (drive field) coil system DF.

Using the MPI excitation coil system DF, it is possible to generate homogeneous AC fields in the kHz range (excitation field=drive field) with the field direction in the Z-direction, as a result of which the field-free line FFL can be moved orthogonally to its position ($\beta+90°$) in the XY-plane. Therefore, this configuration can be used to carry out MPI measurements. Here, the field changes induced by the MPI excitation coil system DF are used to excite magnetic nanoparticles and to detect the particle signal (the projection signal along the FFL). Preferably, two separate coils are used for particle excitation and signal detection. In this case, a dedicated reception coil should be constructed as a gradiometer.

Figure 2:
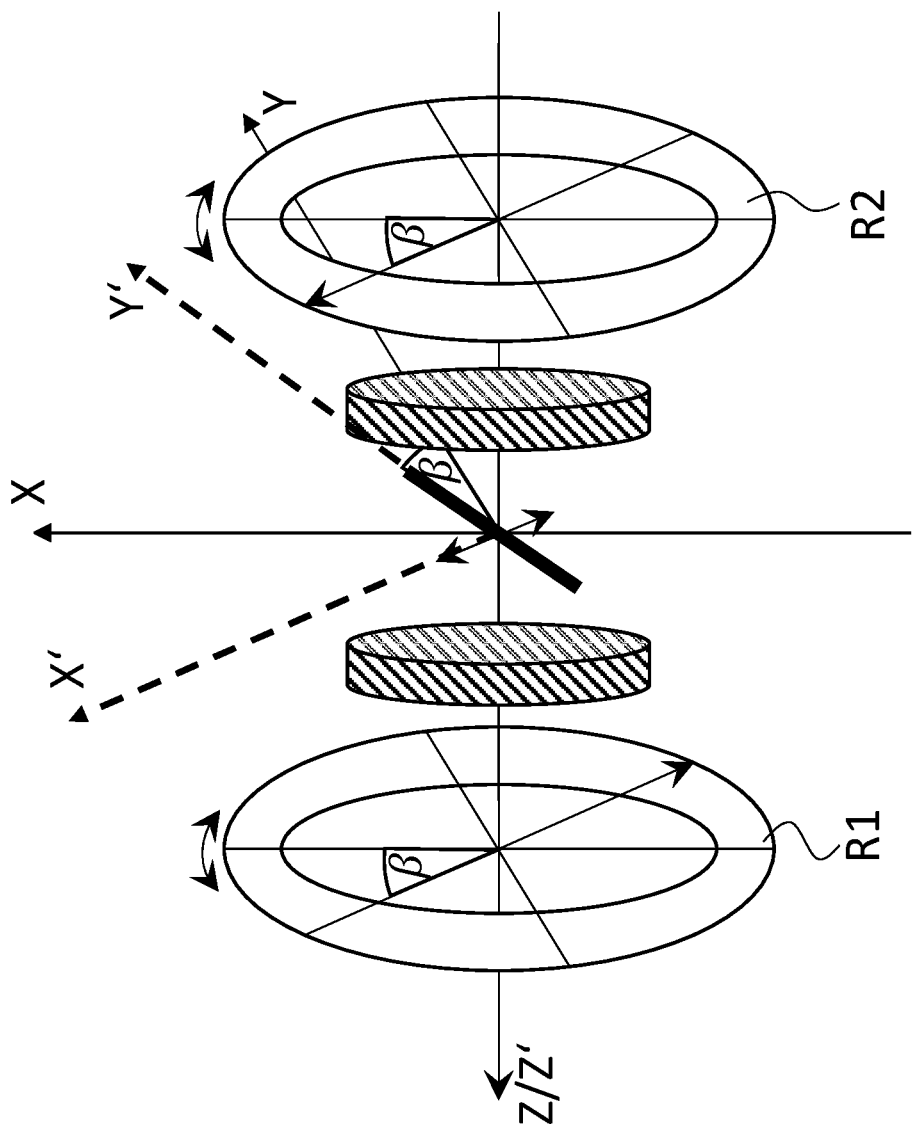
FIG. 2 shows a magnet arrangement and an MPI excitation coil system of a hybrid imaging apparatus according to the invention with antiparallel dipole magnetization directions of the ring magnets in the X'-direction.

In FIG. 1, the dipole magnetization directions of both ring magnets R1, R2 point in the X-direction of a Cartesian coordinate system XYZ. A common rotation through the angle $\beta$ about the common axis of rotation Z by both ring magnets R1, R2 results in a rotation of the field-free line FFL, as shown in FIG. 2. A further coordinate system X'Y'Z' defined by the ring magnets R1, R2 is then twisted through the angle $\beta$ in relation to the coordinate system XYZ, with Z' corresponding to Z. The further coordinate system X'Y'Z' is defined such that the field-free line generated by the magnetic coil pair R1/R2 is always aligned in the Y'-direction.

By adapting the ring magnets R1, R2 (distance, thickness, material, residual magnetism, position, magnetization, internal and external diameter), the MPI magnetic field generated by the ring magnets R1, R2 can be optimized in relation to the amplitude (B1) and the gradient linearity (minimizing the odd field components $B3, B5, \ldots, Bn$).

Figure 3:
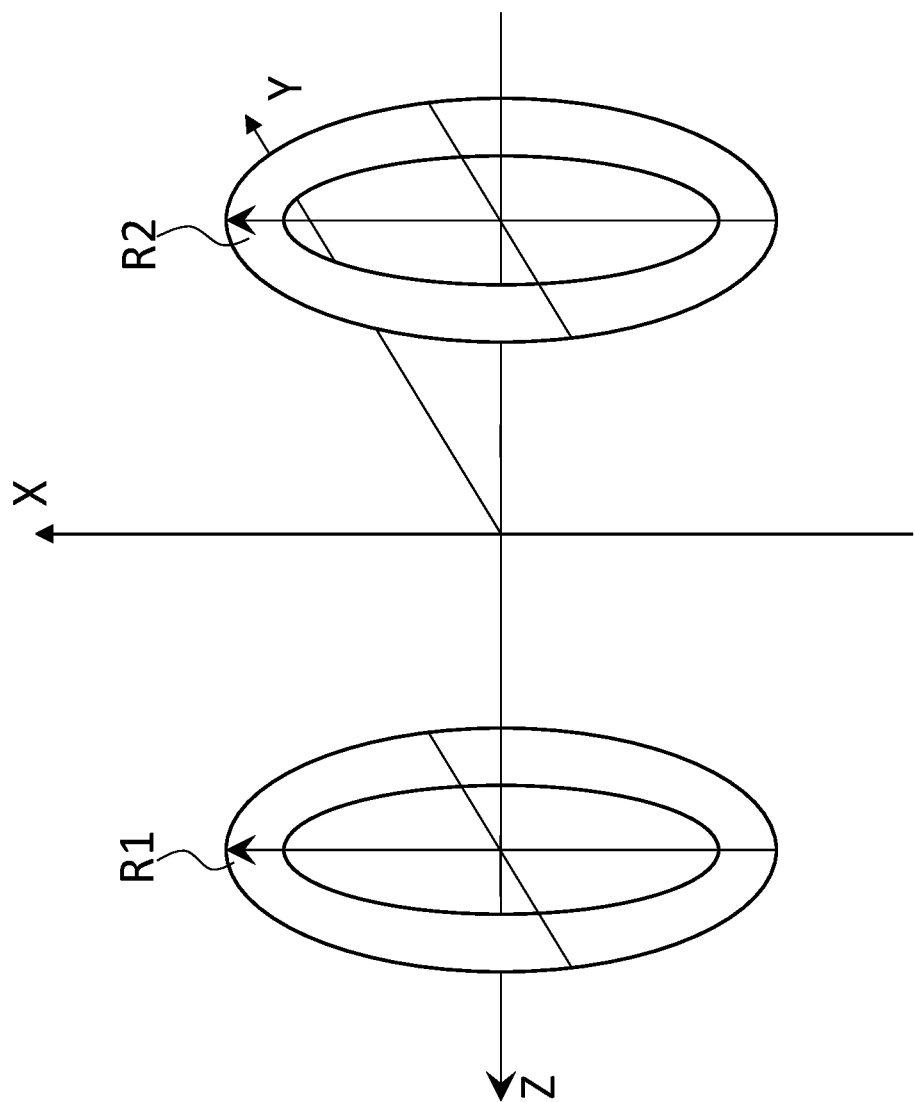
FIG. 3 shows a magnet arrangement of a hybrid imaging apparatus according to the invention with parallel dipole magnetization directions of the ring magnets in the X-direction.

A magnetic field for MRI measurements can also be generated using the same ring magnet pair. To this end, the two ring magnets R1, R2 are brought into a position in which the dipole magnetization directions of the two ring magnets R1, R2 point in the same direction (parallel), as shown in FIG. 3.

With adaptation of the ring magnets R1, R2 (ring spacing, ring thickness, ring material, residual magnetism, ring position, ring magnetization, ring internal and ring external diameter, etc.), it is possible, with the aid of suitable simulation software, to optimize the MRI magnetic field in relation to the amplitude (B0) and the homogeneity by minimizing the even field components $B2, B4, \ldots Bn$.

Thus, the ring magnet pair R1/R2 can be used to generate, firstly, an MPI magnetic field with a gradient B1 for MPI measurements (MPI mode) and, secondly, a homogenous MRI magnetic field for MRI measurements (MRI mode). Merely the two rings R1, R2 have to be twisted against one another about the Z-axis in order to switch between MRI mode and MPI mode. According to the invention, this is used to realize a hybrid imaging apparatus.

Figure 4:
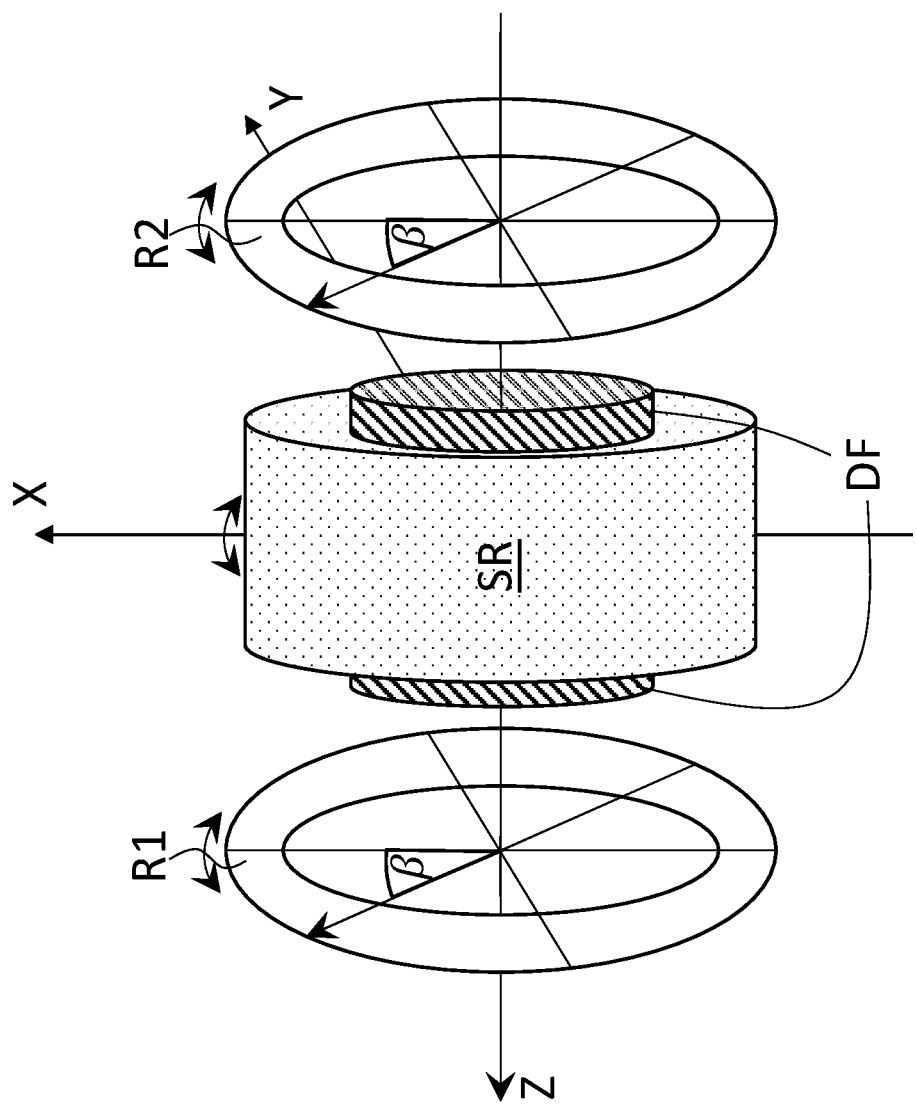
FIG. 4 shows a hybrid imaging apparatus according to the invention with a magnet arrangement, an MRI shim apparatus, and an MRI/MPI excitation coil system.

To facilitate MRI imaging, further components need to be introduced into the hybrid imaging apparatus, e.g., an MRI shim apparatus SR (shim coils, shim tube), an MRI gradient system (not shown), an MRI excitation and detection coil system. FIG. 4 shows a hybrid imaging apparatus according to the invention, which can be operated in the MPI mode and in the MRI mode. In addition to the first ring magnet pair R1/R2 and the MPI excitation coil system DF, the hybrid imaging apparatus shown in FIG. 4 comprises an MRI shim apparatus SR with a shim tube for the basic homogenization of the magnetic field in the MRI mode. The remaining aforementioned MRI components have not been shown in this schematic illustration for reasons of clarity. By way of example, the resonant excitation and detection coils in the MRI mode can be embodied together with the MPI excitation coil system DF. In FIG. 4, the magnetic coil system is in the MRI mode, i.e., the dipole magnetization directions of the two ring magnets R1, R2 are parallel to one another. However, in comparison with the ring magnet pair R1/R2 illustrated in FIG. 3, the two ring magnets R1, R2 in FIG. 3 are twisted together through the angle β about the common axis of rotation Z. This leads to rotation of the B0-field vector in the XY-plane. Thus, a twist of the ring magnet pair R1/R2 allows new MR sequences in which various field directions can be exploited (such as, e.g., susceptibility measurements). Preferably, the shim tube SR and the MRI gradient system are rotated together with the ring magnet pair R1/R2. The MPI excitation coil system DF can also serve as an excitation detection apparatus for the MRI measurements.

Figure 5:
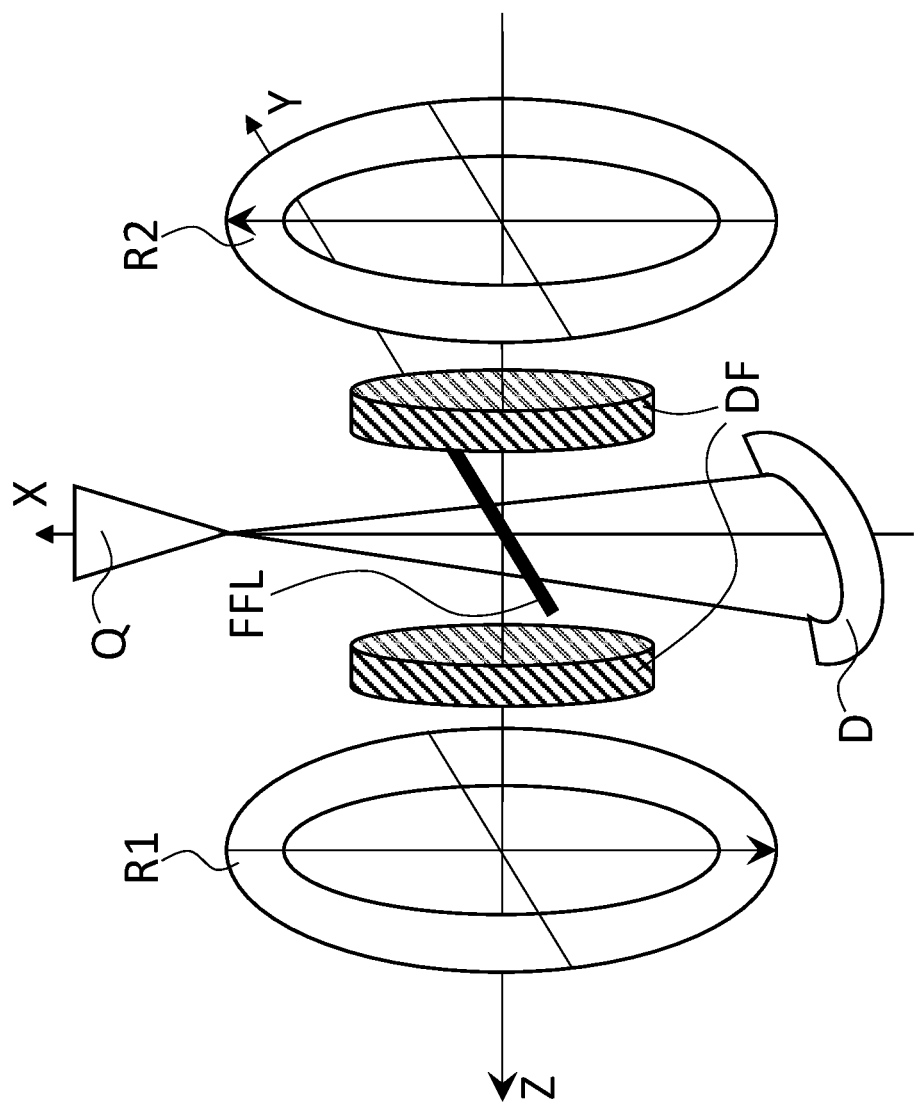
FIG. 5 shows a hybrid imaging apparatus according to the invention with a magnet arrangement, a CT unit, and an MPI excitation coil system.

FIG. 5 shows another embodiment of the hybrid imaging apparatus according to the invention, which can be operated in the MPI mode and in the CT mode. To this end and in addition to the first ring magnet pair R1/R2 and the MPI excitation coil system DF, the hybrid imaging apparatus comprises a CT unit with an x-ray source Q and an x-ray detector D attached on a circle segment opposite the x-ray source Q. The ring magnets R1, R2 of the hybrid imaging apparatus shown in FIG. 5 are in the MPI mode, i.e., the dipole magnetization directions of the two ring magnets R1, R2 are antiparallel such that a magnetic field with a field-free line FFL is generated. The field-free line FFL can be moved in the sample volume PV by means of the MPI excitation coil system. The beam path generated by the x-ray source Q is preferably radiated-in in the plane in which the field-free line FFL is moved (the XY-plane in this case). The angle between the dipole magnetization direction and the beam path axis of the x-ray beam from the x-ray source Q can be defined freely (but preferably to be constant). In the schematic illustration shown in FIG. 5, the orientation is chosen in such a way that the field-free line FFL is perpendicular to the beam path axis and the movement (deflection) of the field-free line FFL, generated by the MPI excitation coil system, is implemented along the beam path (i.e., in the X-direction). This facilitates a simultaneous measurement of MPI data and CT data at the same location. To avoid artifacts in the CT reconstruction, the CT unit should be arranged in such a way that no metallic structures are present in the x-ray beam path generated by the x-ray source Q. This can be achieved by virtue of the MPI excitation coil system comprising two partial coils between which the x-ray beam path extends, as shown in FIG. 5.

Figure 6:
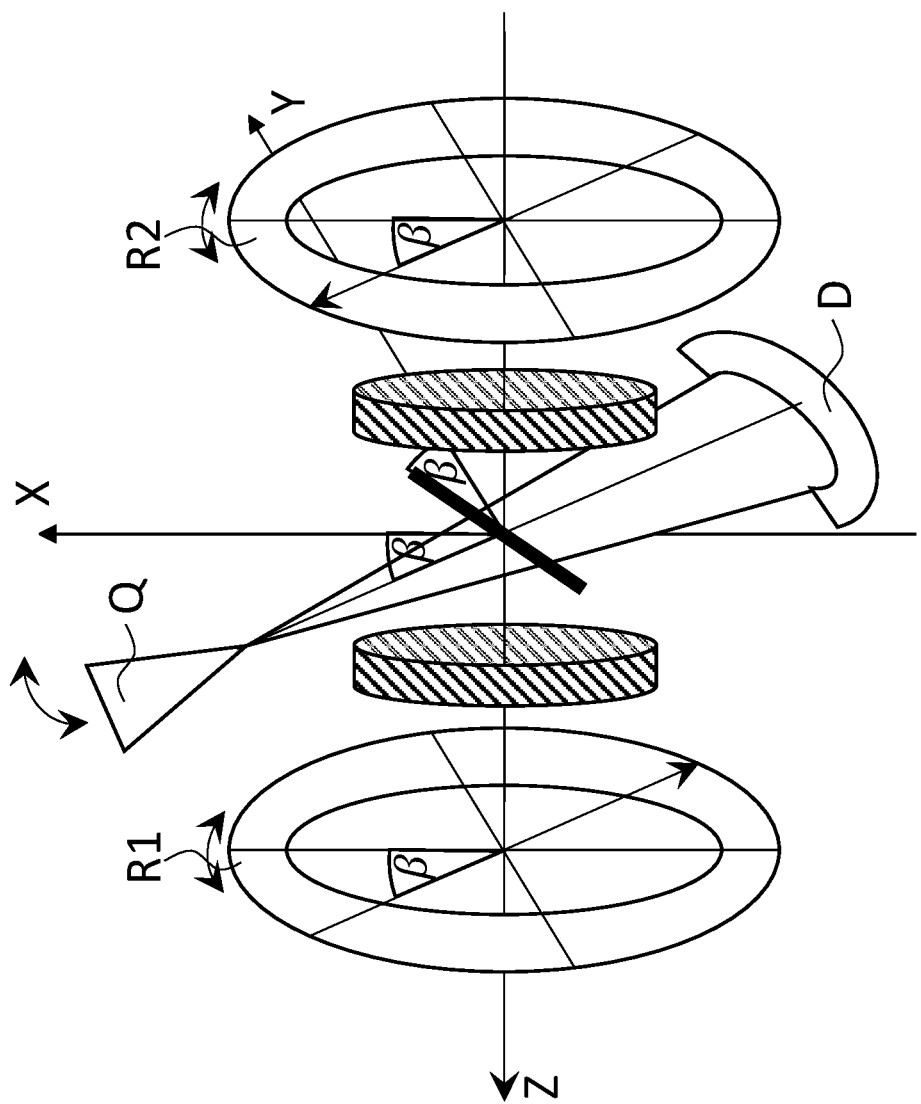
FIG. 6 shows the hybrid imaging apparatus of FIG. 5, wherein the CT unit and magnet arrangement are twisted in relation to the MPI excitation coil system.

A common rotation of both ring magnets R1, R2 through the angle β about the common axis of rotation Z results in a rotation of the field-free line FFL, as shown in FIG. 6. Here, it is advantageous to attach the CT unit in such a way that a common axis of rotation is used for the rotation of the ring magnets R1, R2 and the CT unit. A common rotation of the ring magnets R1, R2 and the CT unit results in a constant magnetic field within the x-ray source Q and consequently leads to constant deflection of the electron beam in the x-ray source; this deflection can be determined in advance and can be taken into account accordingly. In this way, a multiplicity of projections can be determined at the same location using both modalities (MPI mode and CT mode).

Figure 7:
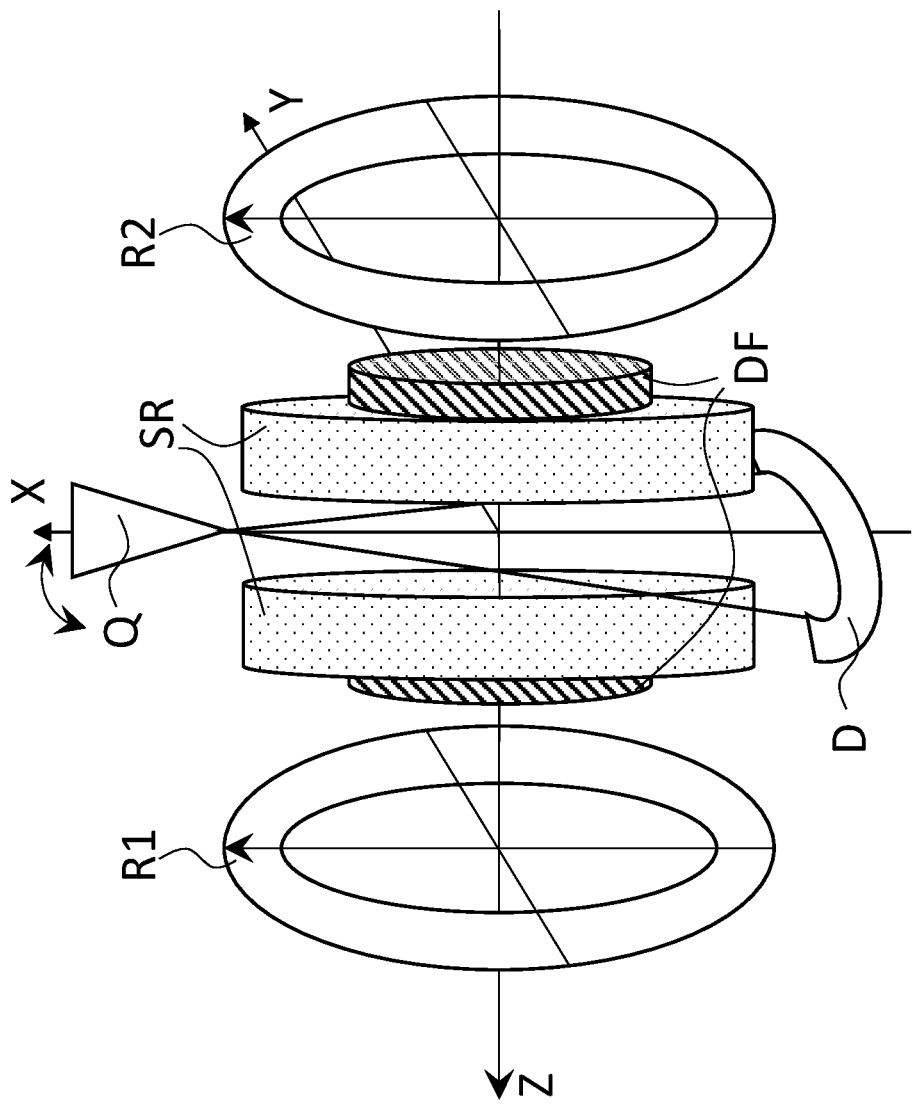
FIG. 7 shows a hybrid imaging apparatus according to the invention with a magnet arrangement, an MRI shim apparatus, CT unit, and an MRI/MPI excitation coil system.

FIG. 7 shows a particularly preferred embodiment of the hybrid imaging apparatus according to the invention, which can be operated in three different imaging modes (MRI mode, CT mode, and MPI mode). The ring magnets R1, R2 are illustrated in the MRI mode, i.e., the dipole magnetization directions of the two ring magnets R1, R2 are parallel to one another. As a result, a homogeneous B0-field is generated in the dipole direction. Both the MPI excitation coil system DF and the shim tube SR have split embodiment in FIG. 7 in order to facilitate an obstacle-free beam path of the x-ray radiation, generated by the x-ray source Q, to the x-ray detector D, independently of the twist angle β of the CT unit in relation to the MPI excitation coil system DF or the shim tube SR.

For the CT mode, it is irrelevant whether the dipole magnetization directions of the two ring magnets R1, R2 are aligned parallel or antiparallel to one another. CT mode and MRI mode or CT mode and MPI mode can therefore be operated in parallel.

The invention claimed is:

1. A hybrid imaging apparatus for imaging an object to be examined located in a sample volume, wherein the hybrid imaging apparatus can be operated in an MPI mode and in at least one further imaging mode and comprises a magnet arrangement embodied to generate, in the MPI mode, a magnetic field with a gradient B1 and a field-free region in the sample volume,
  wherein the magnet arrangement comprises a ring magnet pair with two ring magnets in a Halbach dipole configuration, which are arranged coaxially on a common Z-axis that extends through the sample volume,
  wherein the ring magnets are arranged so as to be twistable relative to one another about the Z-axis, and
  wherein all ring magnets of the magnet arrangement are mechanically couplable such that the magnet arrangement as a whole is rotatable about the Z-axis.

2. The hybrid imaging apparatus as claimed in claim 1, wherein the ring magnets of the ring magnet pair have antiparallel dipole magnetization directions in the MPI mode.

3. The hybrid imaging apparatus as claimed in claim 1, wherein the apparatus comprises an MPI excitation coil system for generating at least one magnetic excitation field.

4. The hybrid imaging apparatus as claimed in claim 1, wherein the apparatus comprises a shift field coil system configured to shift the field-free region along at least one spatial direction within the sample volume in quasi-static fashion or with a shift frequency.

5. The hybrid imaging apparatus as claimed in claim 1, wherein the field-free region is a field-free line in the MPI mode.

6. The hybrid imaging apparatus as claimed in claim 1, wherein the further imaging mode is an MRI mode for recording magnetic resonance imaging images, wherein the magnet arrangement generates a B0-field with a B0-isocenter, suitable for MRI measurements, by virtue of dipole magnetization directions of the ring magnets within the ring magnet pair being aligned perpendicular to the Z-axis in the MRI mode.

7. A method for combined recording of MPI data in the MPI mode and of MRI data in the MRI mode using an apparatus as claimed in claim 6, wherein MPI data and MRI data are recorded in succession and wherein the ring magnets of the ring magnet pair are twisted with respect to one another for the purposes of switching between the MRI mode and MPI mode.

8. The hybrid imaging apparatus as claimed in claim 1, wherein the further imaging mode is a CT mode for recording computed tomography images, wherein the ring magnets of the first ring magnet pair are spaced apart from one another in the Z-direction and the apparatus comprises a CT unit with an x-ray source and an x-ray detector opposite to the x-ray source, wherein the x-ray source and the x-ray detector are mounted in an XY-plane perpendicular to the Z-axis in a manner rotatable about the Z-axis.

9. The hybrid imaging apparatus as claimed in claim 8, wherein the x-ray source and the x-ray detector are mechanically couplable to the magnet arrangement in such a way that the CT unit is rotatable about the Z-axis together with the magnet arrangement.

10. A method for combined recording of MPI and CT data using an apparatus as claimed in claim 9, comprising rotating the magnet arrangement and the CT unit together about the Z-axis.

11. The method as claimed in claim 10, further comprising acquiring MPI and CT data simultaneously.

12. The method as claimed in claim 11, wherein the MPI data are acquired from a 2D MPI acquisition plane of the sample volume, wherein the CT unit generates an x-ray beam in a CT beam path, and wherein the MPI acquisition plane at least partly overlaps with the CT beam path.

13. The method as claimed in claim 10, wherein the combined MPI-CT recording comprises a helical scan, wherein the CT unit is rotated about the Z-axis together with the magnet arrangement and the MPI excitation coil system such that the field-free region rotates while the object to be examined is moved continuously in the Z-direction through the FoV of the hybrid imaging apparatus.

14. A method for combined recording of CT data in the CT mode and of MRI data in the MRI mode using an apparatus as claimed in claim 1, wherein the at least one further imaging mode comprises:
   an MRI mode for recording magnetic resonance imaging images, wherein the magnet arrangement generates a B0-field with a B0-isocenter, suitable for MRI measurements, by virtue of dipole magnetization directions of the ring magnets within the ring magnet pair being aligned perpendicular to the Z-axis in the MRI mode, and
   a CT mode for recording computed tomography images, wherein the ring magnets of the first ring magnet pair are spaced apart from one another in the Z-direction and the apparatus comprises a CT unit with an x-ray source that generates an x-ray beam in a CT beam path and an x-ray detector opposite to the x-ray source, wherein the x-ray source and the x-ray detector are mounted in an XY-plane perpendicular to the Z-axis in a manner rotatable about the Z-axis,
   and wherein the B0-isocenter and the CT beam path partly overlap one another,
   the magnet arrangement, the x-ray source, and the x-ray detector are rotated together about the Z-axis, at least in the CT mode, for the purposes of capturing spatial encoding, and
   CT data and MRI data are acquired sequentially, respectively, in the CT mode and in the MRI mode.

15. A method for designing a magnet arrangement for use in a hybrid imaging apparatus as claimed in claim 6 with an MPI mode and an MRI mode, wherein the magnet arrangement comprises ring magnets with a central bore, the method comprising:
   a. specifying a target magnetic field B0 in the MRI mode and in the MPI mode a target gradient B1 of a magnetic field B to be generated by the magnet arrangement, and specifying a number of said ring magnets and an internal diameter of the central bore of the ring magnets;
   b. specifying a homogeneity of the magnetic field in a sample volume to be generated by the magnet arrangement in the MRI mode by virtue of setting to zero at least a first field order of a mathematical expansion of the magnetic field to be generated by the magnet arrangement, and
      specifying a linearity of the magnetic field in the sample volume to be generated by the magnet arrangement in the MPI mode by virtue of setting to zero at least a second field order of the mathematical expansion of the magnetic field to be generated by the magnet arrangement; and
   c. determining free design parameters, including geometry parameters of the ring magnets and a distance between the ring magnets, by minimizing the volume of the ring magnets according to the constraints of steps a) and b) by means of an optimization process.

* * * * *